US009095450B2

(12) United States Patent
Runco et al.

(10) Patent No.: US 9,095,450 B2
(45) Date of Patent: Aug. 4, 2015

(54) INSERTION INSTRUMENT FOR ANTERIORLY INSERTING INTERVERTEBRAL SPINAL IMPLANTS

(75) Inventors: Thomas J. Runco, Providence, RI (US); John Mulcahy, Chester Springs, PA (US); Seungkyu Daniel Kwak, Needham, MA (US)

(73) Assignee: DePuy Syntheses Products, Inc., Raynham, MA (US)

( * ) Notice: Subject to any disclaimer, the term of this patent is extended or adjusted under 35 U.S.C. 154(b) by 1221 days.

(21) Appl. No.: 12/343,775

(22) Filed: Dec. 24, 2008

(65) Prior Publication Data
US 2010/0160983 A1   Jun. 24, 2010

(51) Int. Cl.
*A61B 17/70* (2006.01)
*A61F 2/46* (2006.01)
*A61F 2/44* (2006.01)
*A61F 2/30* (2006.01)

(52) U.S. Cl.
CPC .............. *A61F 2/4611* (2013.01); *A61F 2/4465* (2013.01); *A61F 2002/30841* (2013.01); *A61F 2002/4475* (2013.01); *A61F 2002/4622* (2013.01); *A61F 2002/4627* (2013.01)

(58) Field of Classification Search
CPC ....... A61F 2/46; A61F 2/4603; A61F 2/4611; A61F 2002/4623; A61F 2002/4625; A61F 2002/4627
USPC .......... 606/86 A, 279, 90, 95, 96, 98, 99, 102
See application file for complete search history.

(56) References Cited

U.S. PATENT DOCUMENTS

| | | | |
|---|---|---|---|
| 3,486,505 A | | 12/1969 | Morrison |
| 5,258,007 A | * | 11/1993 | Spetzler et al. ............... 606/208 |
| 5,431,658 A | | 7/1995 | Moskovich |
| 5,720,751 A | * | 2/1998 | Jackson ...................... 606/86 R |
| 5,782,830 A | * | 7/1998 | Farris .............................. 606/99 |
| 5,899,901 A | * | 5/1999 | Middleton ..................... 606/914 |
| 6,159,215 A | | 12/2000 | Urbahns |
| 6,224,607 B1 | * | 5/2001 | Michelson ....................... 606/96 |
| 6,319,257 B1 | * | 11/2001 | Carignan et al. ................ 606/99 |
| 6,478,800 B1 | * | 11/2002 | Fraser et al. ..................... 606/99 |
| 7,320,689 B2 | * | 1/2008 | Keller .............................. 606/99 |
| 7,722,613 B2 | * | 5/2010 | Sutterlin et al. ................. 606/79 |
| 7,722,622 B2 | * | 5/2010 | Evans et al. ..................... 606/99 |
| 2002/0116009 A1 | * | 8/2002 | Fraser et al. ..................... 606/99 |
| 2004/0220567 A1 | * | 11/2004 | Eisermann et al. ............. 606/61 |
| 2004/0220582 A1 | * | 11/2004 | Keller .............................. 606/99 |
| 2005/0021042 A1 | * | 1/2005 | Marnay et al. .................. 606/99 |
| 2005/0113842 A1 | * | 5/2005 | Bertagnoli et al. ............. 606/90 |
| 2005/0165408 A1 | | 7/2005 | Puno |
| 2006/0074425 A1 | * | 4/2006 | Sutterlin et al. ................ 606/79 |
| 2006/0167461 A1 | * | 7/2006 | Hawkins et al. ................ 606/90 |
| 2006/0195097 A1 | | 8/2006 | Evans |
| 2007/0118145 A1 | * | 5/2007 | Fischer et al. ................... 606/99 |
| 2010/0121385 A1 | * | 5/2010 | Blain et al. .................. 606/86 A |
| 2010/0262199 A1 | * | 10/2010 | Wallenstein et al. ....... 606/86 A |
| 2010/0331988 A1 | * | 12/2010 | Marnay et al. ............. 623/17.16 |

OTHER PUBLICATIONS

DePuy AcroMed Inc. Keystone Graft Instruments Surgical Technique, 2000.
DePuy AcroMed Inc. Universal ALIF Instrument Set Product Guide, 2001.

* cited by examiner

*Primary Examiner* — Ellen C Hammond
*Assistant Examiner* — Christina Negrellirodrigue

(57) ABSTRACT

An implant inserter for use in ALIF spine surgery, wherein the inserter has a flexible bracket, biased closed, onto which two long blades can be removably attached.

31 Claims, 19 Drawing Sheets

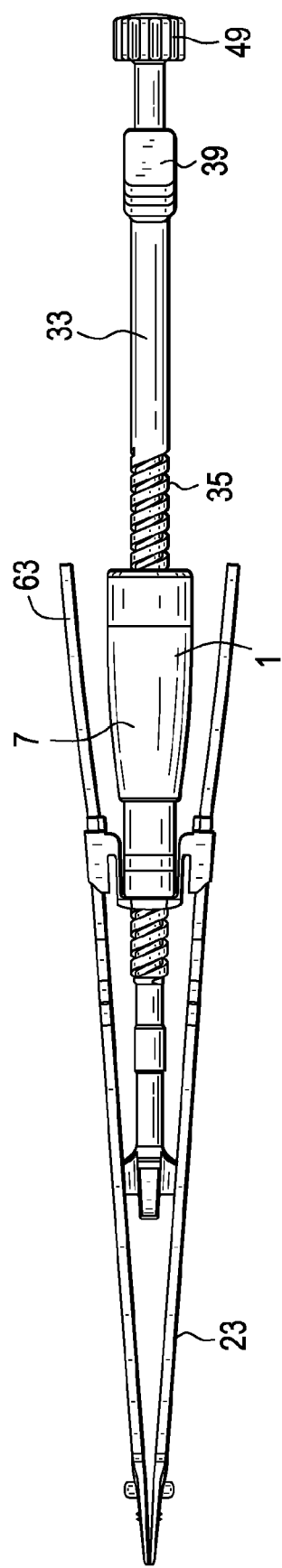

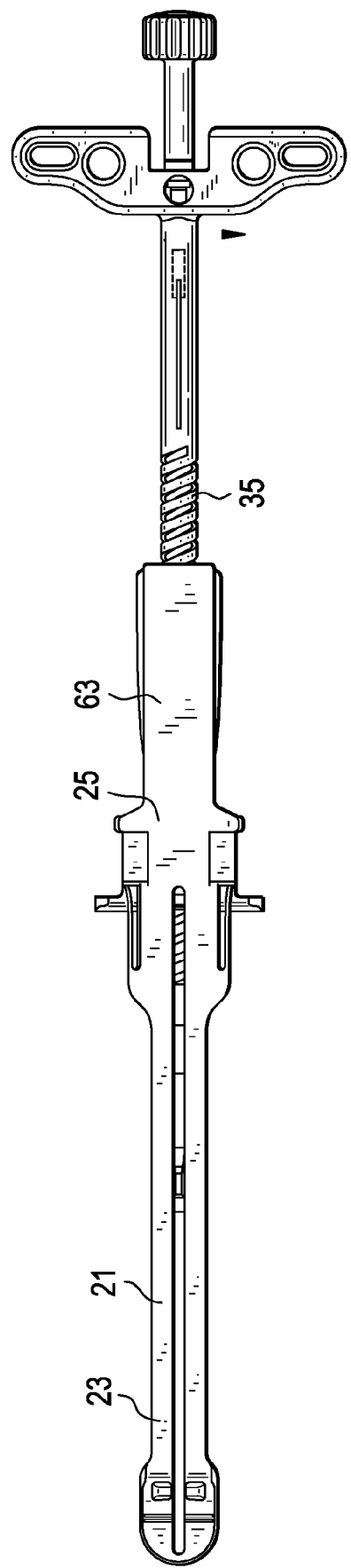

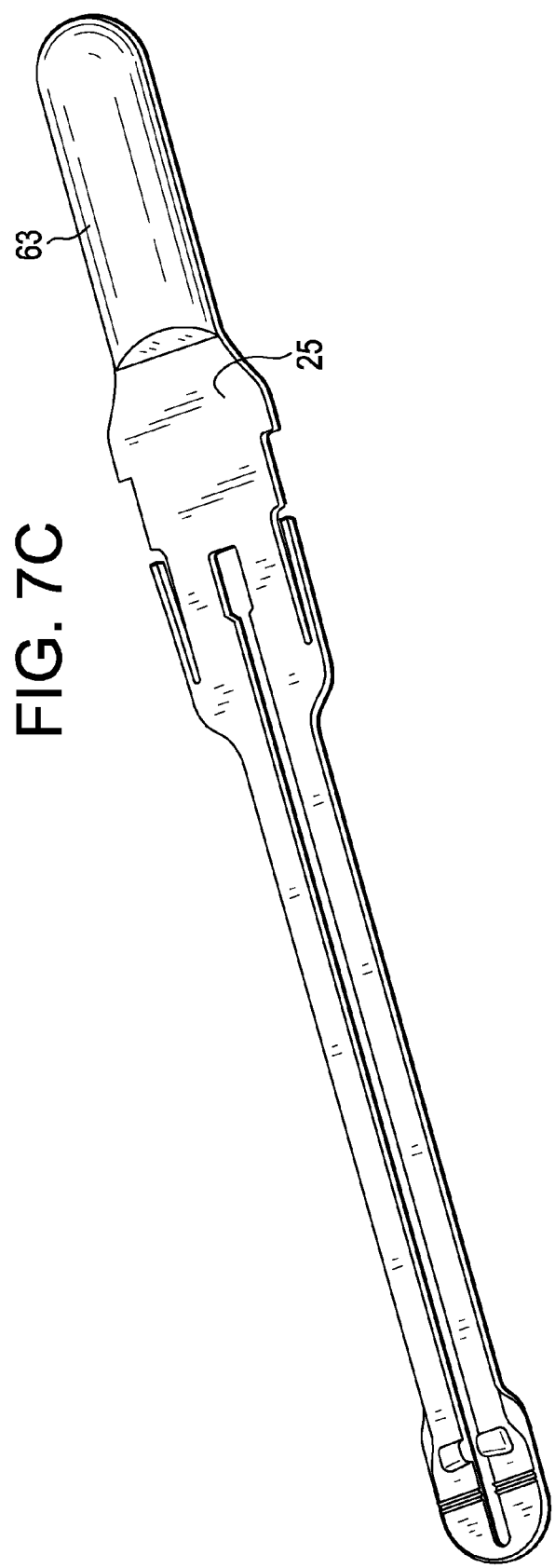

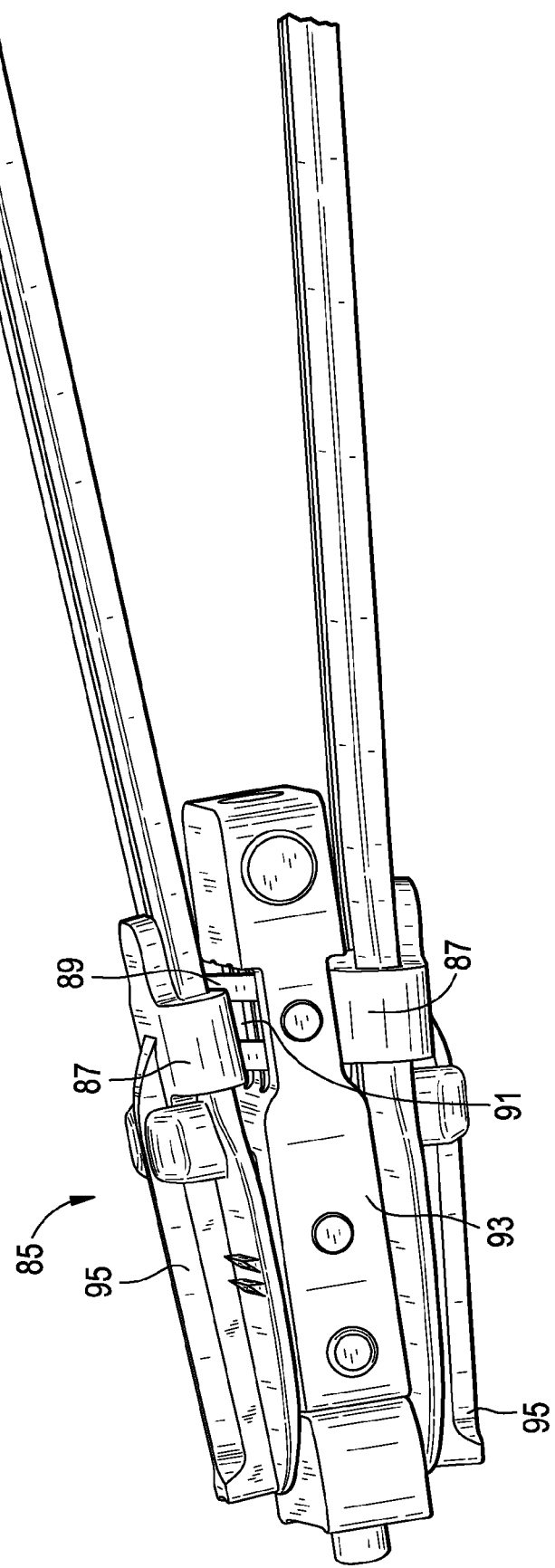

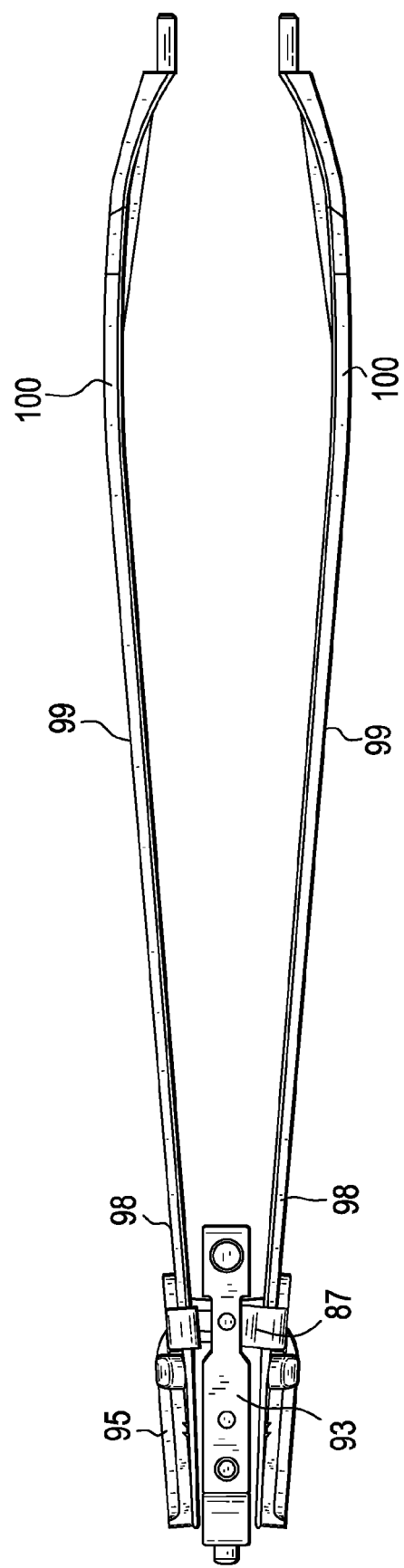

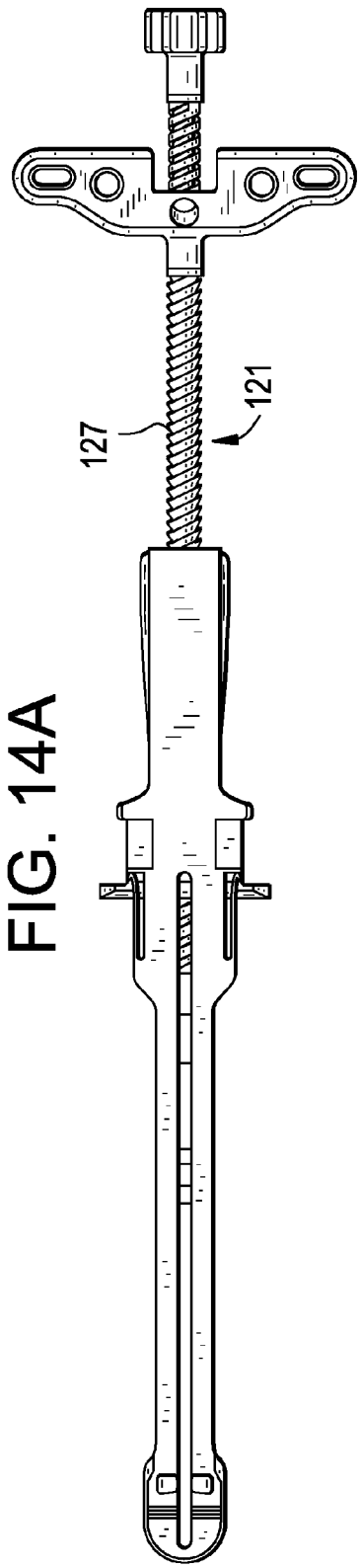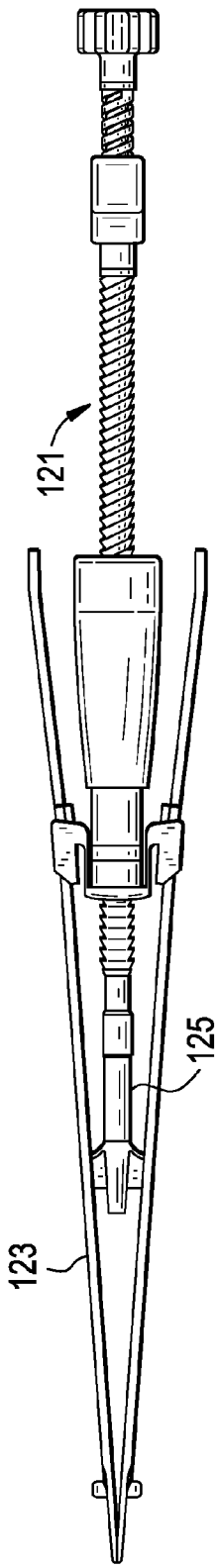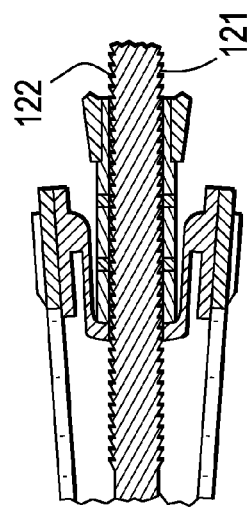

INSERTION INSTRUMENT FOR ANTERIORLY INSERTING INTERVERTEBRAL SPINAL IMPLANTS

BACKGROUND OF THE INVENTION

Current methods for placing bone graft and other implants into the anterior spine—e.g., for Anterior Lumbar Interbody Fusion—are widely varied, and each method comes with its limitations.

U.S. Pat. No. 3,486,505 (Morrison) discloses an instrument to distract two closely adjacent vertebral bodies and at the same time insert an implant between the distracted vertebral bodies. The instrument acts as a protective guide and channel to the inserted implant and at the same time acts as a protective retractor to adjacent soft tissues.

US Published Patent Application No. US 2005/0165408 (Puno) discloses an instrument for inserting an implant in a space between adjacent bony portions including upper and lower guide members separated by a spreader with the implant positioned forwardly of the spreader. The spreader is movable forwardly between the guide members with a drive member to position the implant in a space between the bony portions. The spreader contacts the adjacent bony portions to facilitate withdrawal of the inserter instrument when the implant is positioned in the space.

US Published Patent Application US 2006/0195097 (Evans) discloses an apparatus for use with a spinal implant including a handle structure with a passage. A shaft with a screw thread is moveable within the passage in the handle structure. A pusher block is linked to the shaft, and has a forward surface configured to engage the spinal implant. A screw-threaded clutch member is supported on the handle structure for movement into and out of engagement with the screw thread on the shaft.

The DePuy Spine "Oz Inserter" and associated Pusher Blocks are described in the Technique Guide for the Universal ALIF Instrument Set. This Inserter Assembly is comprised of two long rigid blades (or ramps) that are pivotably connected at a (variable) distance apart. The distal blade tips can be placed into the disc space, while an inserter shaft can be advanced between the blades and towards the distal blade tips. A pusher block on the end of the inserter shaft can thereby advance the implant towards the blade tips and into the intervertebral body disc space. Advancing the inserter shaft and pusher block serves to spread the blades apart and to open the disc space for placement of the implant. The blades can also be used as a spreader by virtue of their pivot point, as the surgeon squeezes the blade handles to provide additional distraction of the disc space.

The DePuy Spine Keystone Blades are described in the Technique Guide for the Keystone Graft Instruments. There are two types of Keystone ramps (or blades) described, with the standard ramps consisting of flat metal blades that are flexibly connected at their proximal end. The blade tips are inserted into an intervertebral body disc space, and an implant can be pushed distally into the disc space by means of an inserter shaft which holds the graft. Impaction of the graft implant serves to spread the ramps apart as the implant is advanced into the disc space. There is also a Modular Insertion Ramp instrument, whereby the flat blades are assembled to an adjustable handle. The handle can be opened up to allow the graft to fit between the ramp blades. Again, the implant can be pushed distally towards the disc space by means of a pusher, while Impaction of the graft serves to spread the ramps apart. The ramps are them removed by rocking and pulling them out while leaving the implant in place.

SUMMARY OF THE INVENTION

The current invention seeks to provide an instrument which can deliver an implant into the anterior spine, while also providing some additional features that address certain of the limitations of the existing methods and devices.

In accordance with the present invention, there is provided a vertebral body implant inserter, comprising:
 a) a elongated central body having a distal end, a proximal end, an outer surface, a longitudinal throughbore therethrough, and a pair of spring members (such as leaf springs) extending from the outer surface,
 b) a pair of blades having a distal end portion and a proximal end portion, the proximal end portion of each blade detachably coupled to a respective spring member,
 c) a shaft slidable within the throughbore, the shaft having an outer surface having a threadform thereon.

Also in accordance with the present invention, there is provided a vertebral body implant inserter, comprising:
 a) a elongated central body having a distal end, a proximal end, an outer surface, a first longitudinal throughbore therethrough,
 b) a bracket having i) an intermediate portion having a second longitudinal throughbore therethrough, ii) a first endportion, and iii) a second endportion, each endportion forming a spring member (such as a leaf spring), the intermediate portion contacting the distal end of the central body so that the first longitudinal throughbore aligns with the second longitudinal throughbore,
 c) a pair of blades having a distal end portion and a proximal end portion, the proximal end portion of each blade detachably coupled to a respective spring member,
 d) a shaft slidably advanceable within the first longitudinal throughbore, the shaft having an outer surface having a threadform thereon.

Advantages of the present invention include: providing the ability to distract; protecting the implant from contact with tissue during delivery; controlling the motion of the implant during delivery and allowing impaction of the implant; providing smooth delivery of the implant; controlling the motion of the blades after delivery; and providing a means for extracting the instrument after implant delivery.

DESCRIPTION OF THE FIGURES

FIGS. 7a-7c disclose side and top views of the inserter of the present invention, wherein the blades have proximally extending handle extensions, along with a perspective view of a blade with a handle extension.

FIGS. 14a-14c disclose various views of a third embodiment of a shaft-pusher rod design.

DETAILED DESCRIPTION OF THE INVENTION

Figure 1:
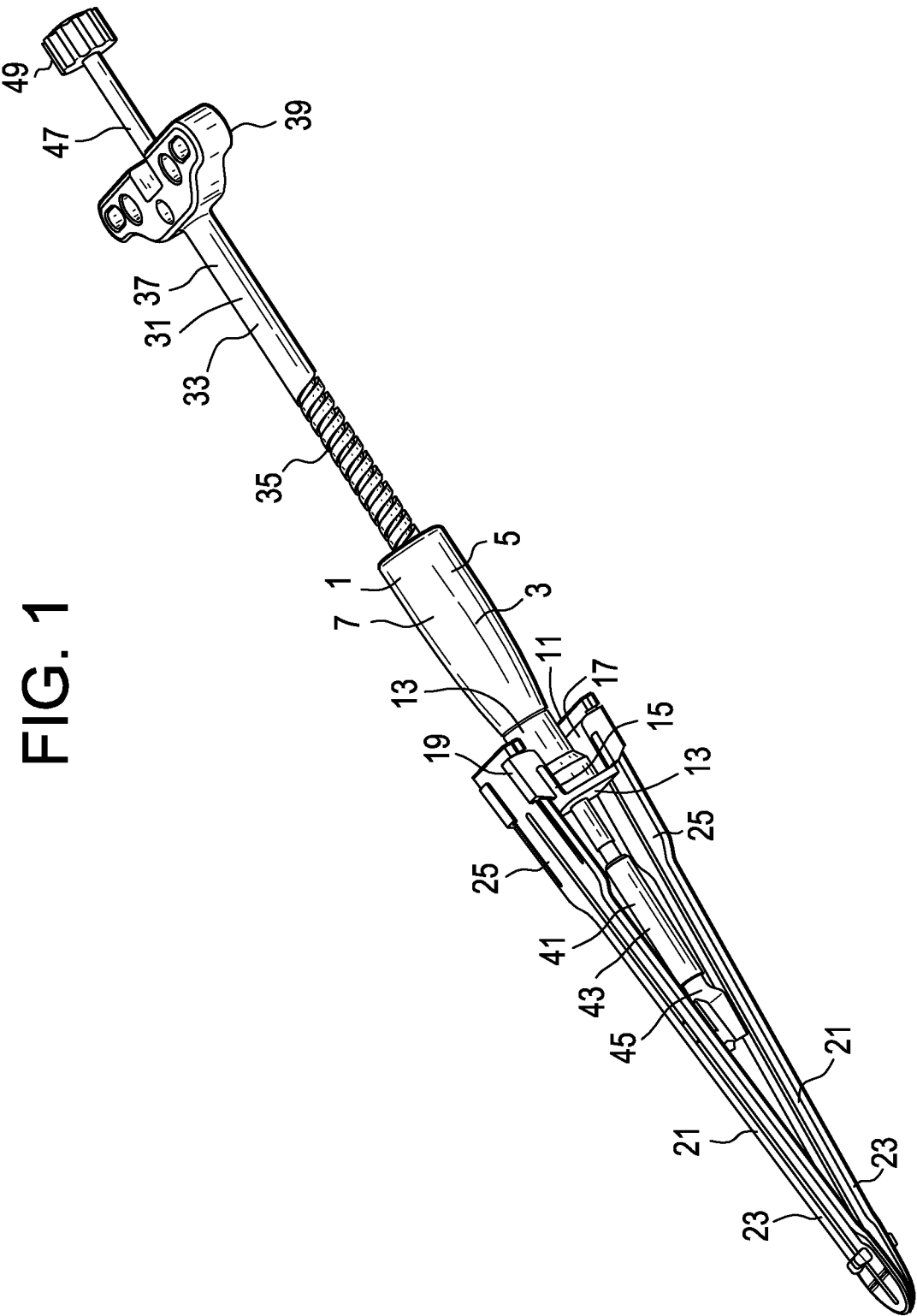
FIG. 1 discloses a perspective view of the inserter of the present invention.

Now referring to FIG. 1, there is provided a vertebral body implant inserter, comprising:
- a) an elongated central body 1 having a distal end 3, a proximal end 5, an outer surface 7, a first longitudinal throughbore therethrough (not shown),
- b) a bracket 11 having i) an intermediate portion 13 having a second longitudinal throughbore therethrough (not shown), ii) a first endportion 15, and iii) a second endportion 17, each endportion forming a leaf spring 19, the intermediate portion contacting the distal end of the central body so that the first longitudinal throughbore aligns with the second longitudinal throughbore,
- c) a pair of blades 21 having a distal end portion 23 and a base portion 25, the base portion of each blade detachably coupled to a respective leaf spring,
- d) a cannulated outer shaft 31 slidable within first longitudinal throughbore, the shaft having an outer surface 33 having a first threadform 35 thereon that mates with a second threadform or teeth (not shown) within the first longitudinal throughbore of the central body and a proximal end 37 forming a first handle 39, and
- e) a pushing rod 41 slidable within the cannula of the shaft, the rod having a distal end 43 forming a pusher block 45 and a proximal end 47 forming a second handle 49.

Figure 2:
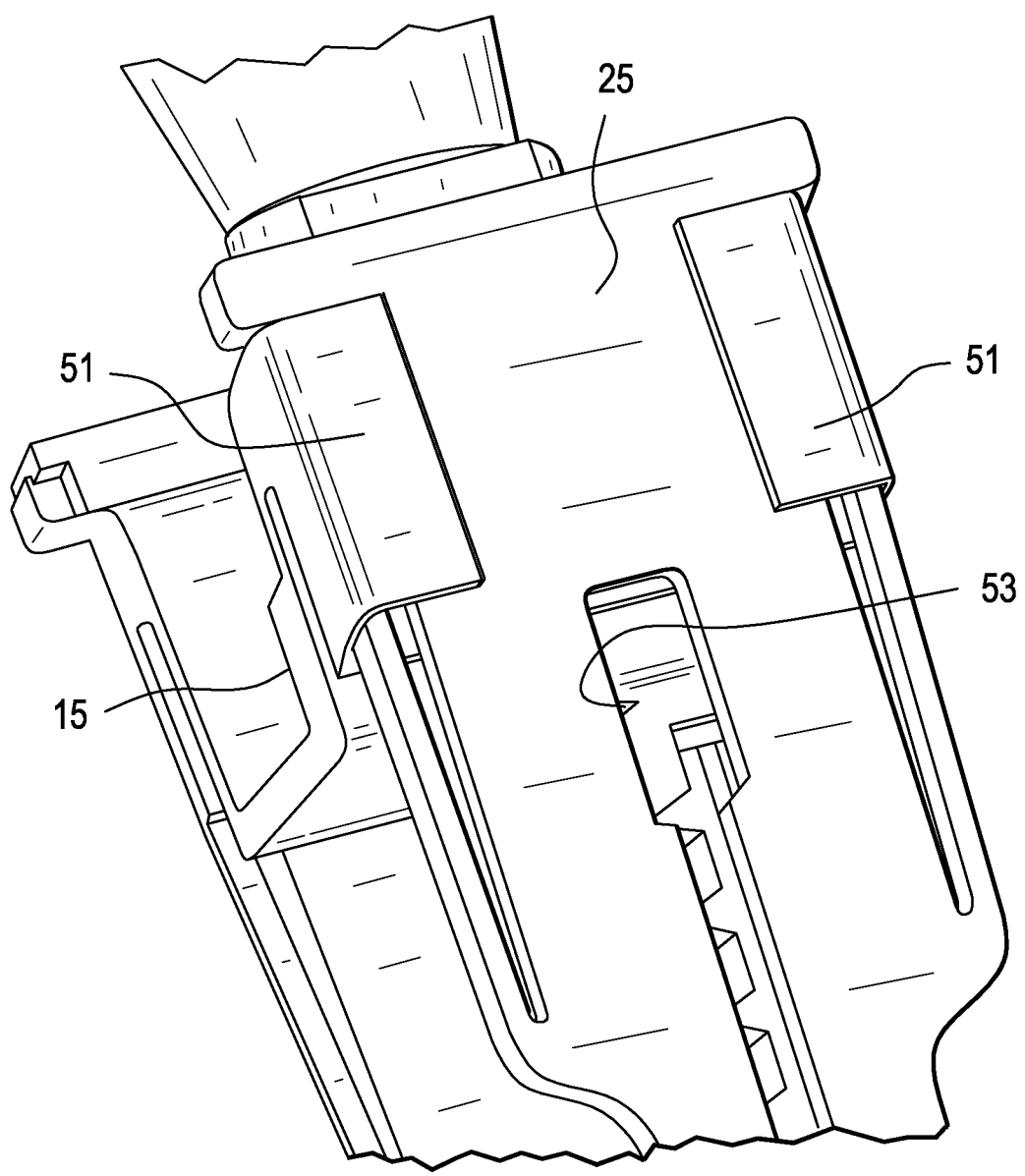
FIG. 2 discloses a magnified view of the bracket-blade assembly of FIG. 1.

The heart of the instrument is a flexible bracket onto which two long blades can be removably attached. Now referring to FIG. 2, each end portion 15 of the bracket may form a pair of prongs 51 that form a clip for detachable release of the blades. The intermediate portion of the bracket assembly includes a second longitudinal throughbore therethrough 53, which allows a shaft to fit through; and the shaft can be used to urge or push the implant forward. The shaft may be threaded through the bracket assembly to advance the implant by threading; or it may allow impaction through the bracket assembly to advance the implant; or it may allow both functions, as desired.

Figure 3:
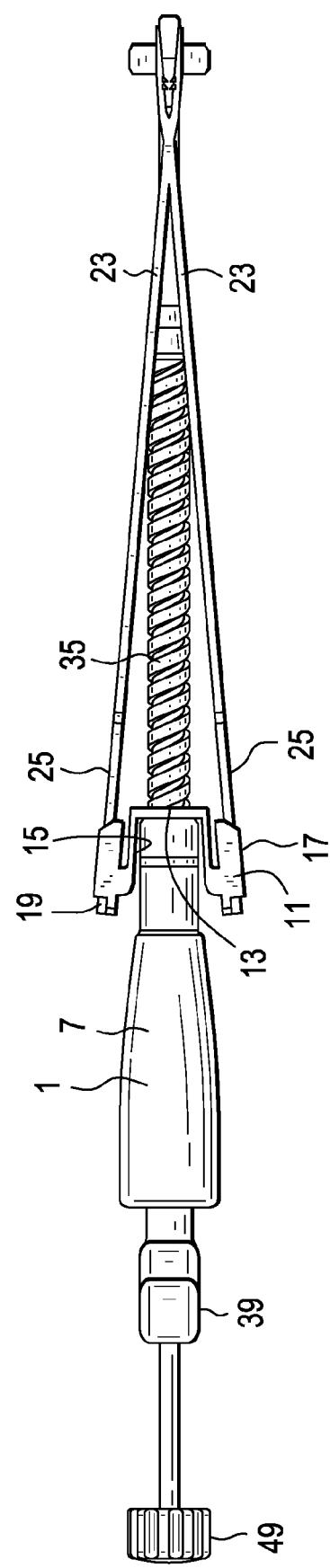
FIG. 3 discloses a side view of the inserter of the present invention, wherein the bracket is biased closed.

Now referring to FIG. 3, in preferred embodiments, the bracket is biased closed. The bracket assembly may also include a handle portion (not shown), extending proximally from the first and second endportions or base portions 25 of the bracket, by which to grasp the instrument.

Figure 4:
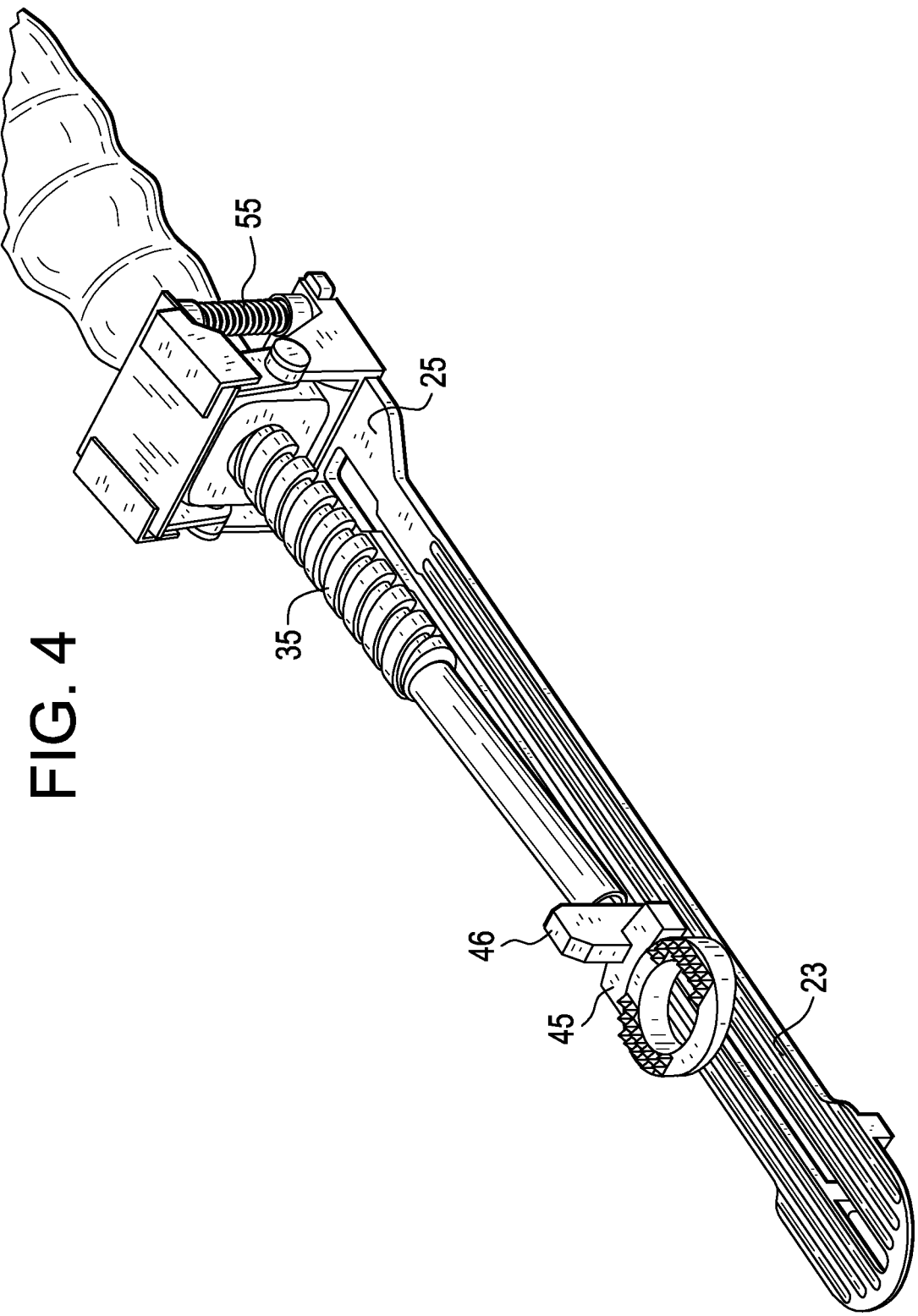
FIG. 4 discloses a perspective view of another embodiment of the inserter of the present invention, wherein the bracket is spring-loaded.

Now referring to FIG. 4, in another embodiment, the bracket assembly could have a spring-loaded actuator 55 rather than made as one continuous spring member.

Figure 5:
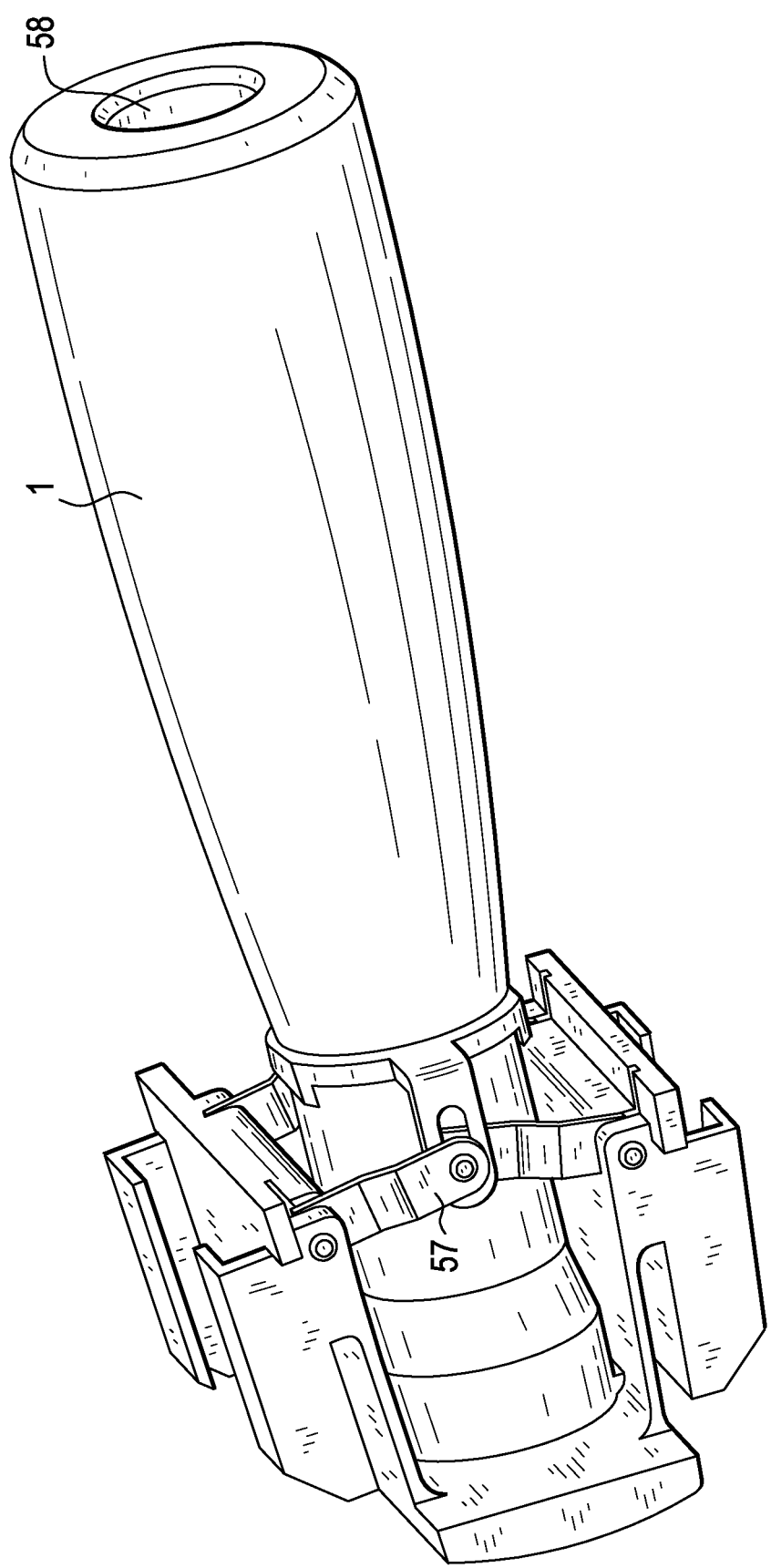
FIG. 5 discloses a perspective view of another embodiment of the inserter of the present invention, wherein the bracket comprises a centering linkage.

Now referring to FIG. 5, in another embodiment, the bracket assembly could have a centering linkage 57 attached to the central body. FIG. 5 also shows the first longitudinal throughbore 58 of the central body.

Figure 6:
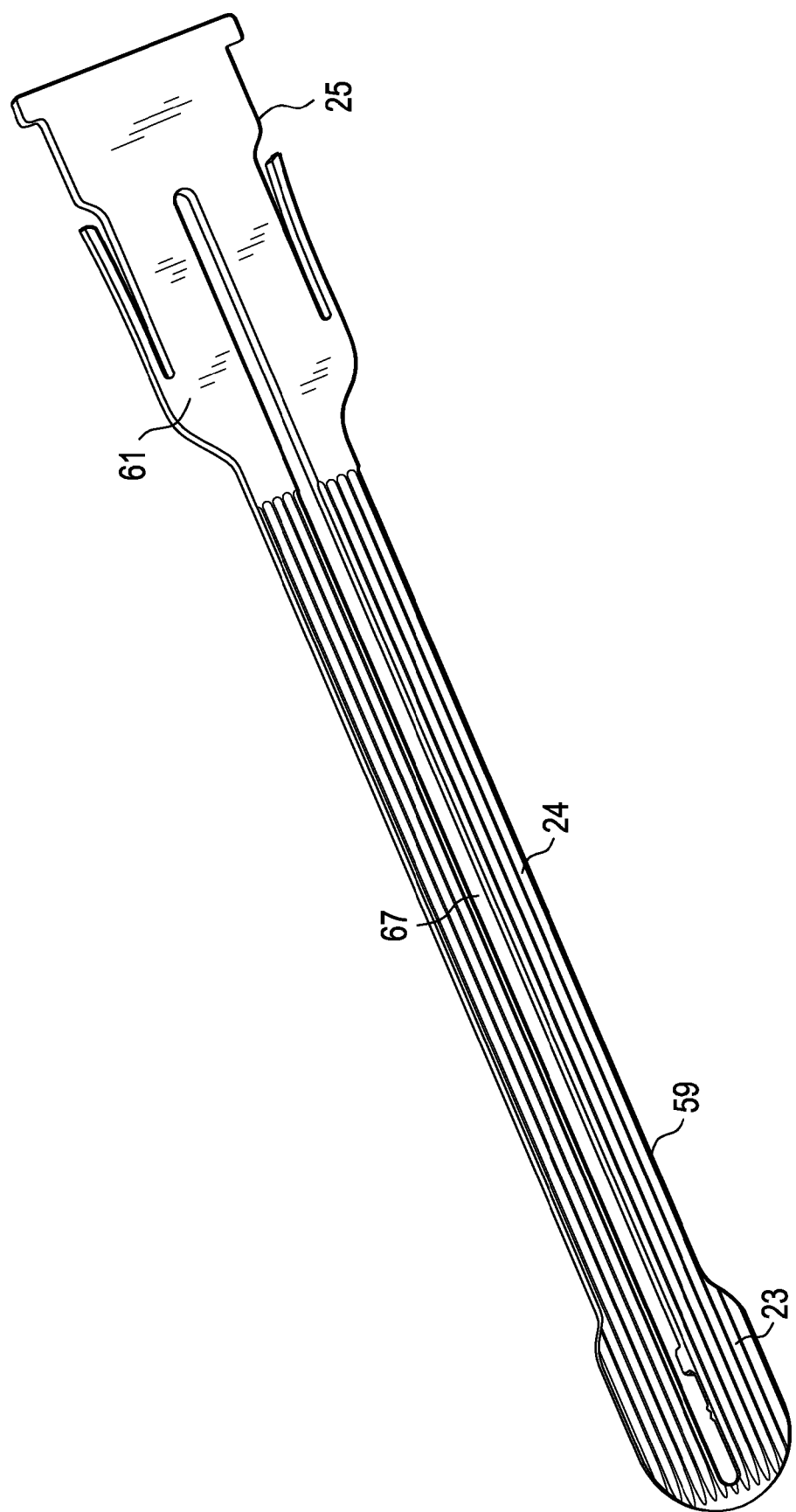
FIG. 6 discloses a perspective view of a blade of the present invention.

The blades of the present invention can be fairly rigid, but connected via a flexible hinge point and biased in the closed direction. The blades are easily and independently removable, but push against each other to hold the implant. Now referring to FIG. 6, the blades do not have uniform width but rather may become wider at their distal tips 23 where they spread the bones apart. That is, each blade further has an intermediate portion 24, and wherein the distal end portion 23 has a width that is greater than a width of the intermediate portion 24. The blades can provide distraction, and tactile feedback, by virtue of their rigidity and their pivoting.

The blades are easily removable, such that different blades can be used for different applications or implants; and they can contain grooves 59 on the inside surface 61 to keep the implant centered during insertion. Alternatively, they can contain raised ridges (not shown) on the inside surface 61 to keep the implant (which would have a corresponding groove) centered during insertion. In one preferred embodiment, in which the blade has a central raised ridge, the implant is an ALIF implant having a corresponding central groove.

Further, and now referring to FIGS. 7a to 7c, the blades of the present invention can also include handle extensions 63 that extend proximally from the base portion 25, which can be used for grasping the instrument. These extended handles can replace the fixed handle on the bracket discussed above. More importantly, the blade's handle extensions 63 can be used to provide distraction when desired, whereby squeezing the handle extensions causes the blades to pivot about the flexible bracket component. Furthermore, as the implant is advanced—and the blade tips move apart—the blade handle extensions will provide some tactile feedback as they angulate toward each other.

Another feature of this device is that the blades can be constrained to be "centered" about the central axis or plane of the bracket assembly, such that they must open and close together, or symmetrically about the central body.

It is also worth noting that the blades themselves can have a certain amount of inherent flexibility, which may be controlled by their thickness and width. Now referring to FIG. 8, the tips 65 of the blades can have a non-uniform thickness—so that they are thinner at the very ends where they contact each other. This narrowing taper on tip 65 allows them to fit into a narrower space when they are brought together (i.e. closed).

Figure 8:
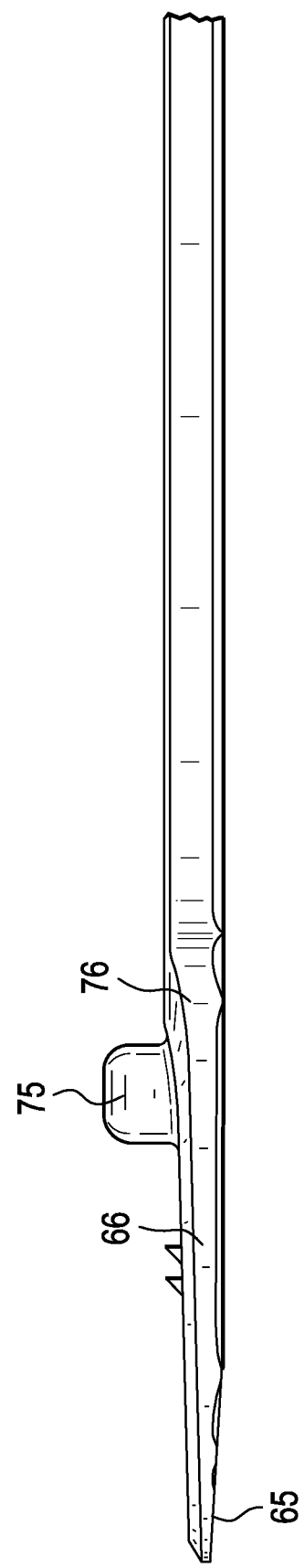
FIG. 8 discloses a side view of a blade having a distally narrowing tip and a vertebral stop.

Also in FIG. 8, the distal end portion of each blade has at least one tooth 66 extending transversely from its outer surface 76 and distal to the vertebral stop 75. These teeth help anchor the blade in the vertebral body.

Referring back to FIG. 6, in some embodiments, each blade has a slot 67 therethrough to help guide the implant. In other embodiments, however, and now referring to FIG. 9a, the blades do not possess the slot, but rather has a substantially planar inner surface 61.

Figure 9A:
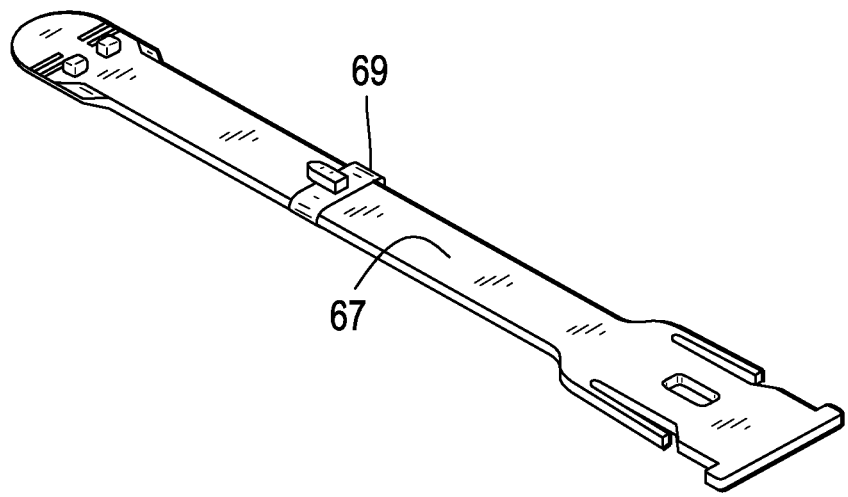
FIGS. 9a-c disclose various views of a blade of the present invention having a first embodiment of a sliding pusher bracket.
Figure 9B:
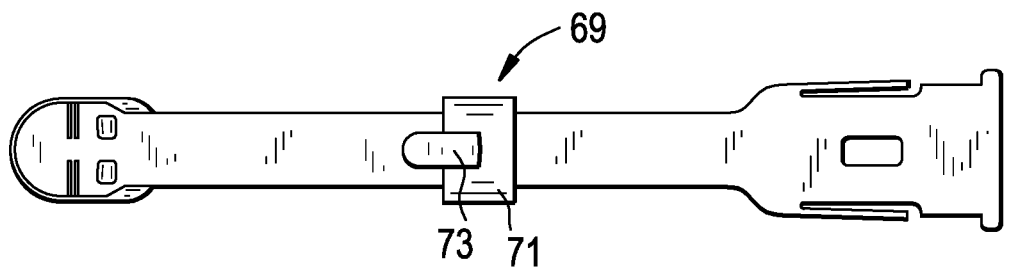
Figure 9C:
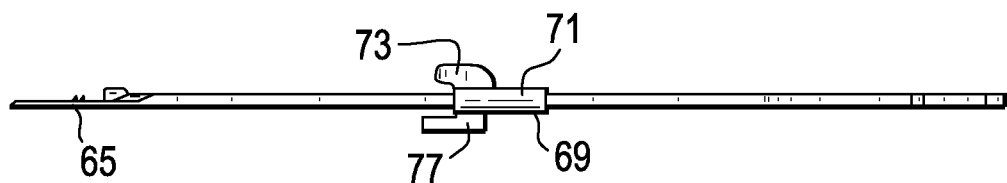

The present invention also provides a mechanism to push the blades out of the interbody space, without needing a slot in the blades. Referring to FIGS. 9a-9c, the inserter may possess a sliding pusher-bracket 69, which bears against the implant between the blades. Each pusher bracket has an annular ring 71 that wraps around the blade and a vertebral stop, or fin, 73 protruding from the ring to contact the vertebral body. As shown in FIGS. 9a-c, the sliding pusher bracket contains a central outer keel (or fin) for pushing against the vertebral body, and the bracket also wraps around the blades rather than having a keel which extends through a central slot in the blades. In this way, the device can push the blades out of the interbody space as the sliding pusher bracket is driven forward by the pusher block—without the need for a slot in the blades. The pushing rod-bracket concept disclosed herein may also eliminate the need for various sizes of conventional pusher blocks.

In some embodiments, the blades of the present invention are pivotally mounted. In other embodiments, the blades of the present invention are flexibly mounted.

In some embodiments, the shaft may be cannulated to allow a pushing rod 41 to pass through the middle of it, whereby the distal end 43 of the pushing rod may contain a pusher block 45. The pusher block can bear against the implant, to push it forward. Advancing the shaft (which may be threaded) can advance the pushing rod and its pusher block, which in turn advances the implant forward.

Alternatively, if the pushing rod is sufficiently longer than the shaft, it can slide back and forth within the shaft, allowing the back of the pushing rod to be directly impacted forward for some distance. The shaft can subsequently be advanced until it once again bears against a portion the pushing rod and/or pusher block, so that it can resume pushing the implant forward.

Therefore, in some embodiments, the shaft has an outer surface having a first threadform thereon, and the throughbore of the central body has a second threadform, wherein the first threadform or set of teeth of the shaft mates or engages with the second threadform within the throughbore.

Figure 11A:
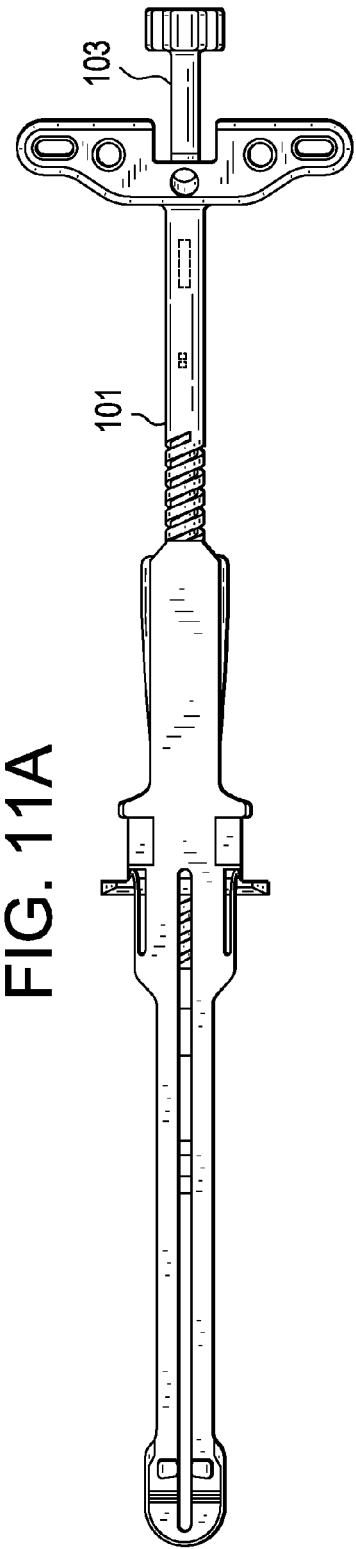
FIGS. 11a-11c disclose various views of a first embodiment of a shaft-pusher rod design.
Figure 11B:
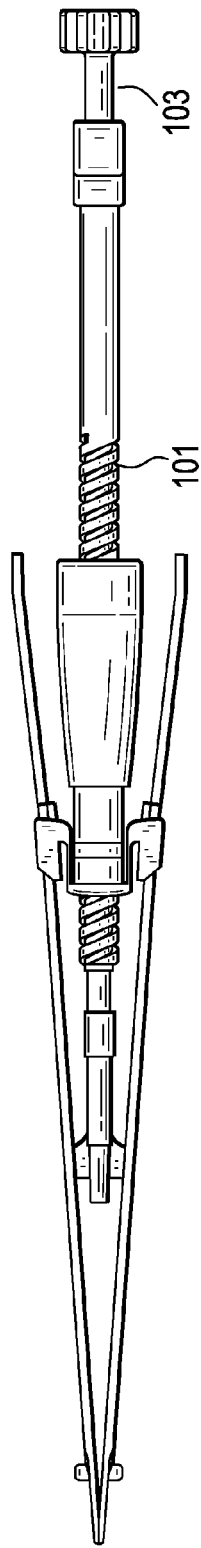
Figure 11C:
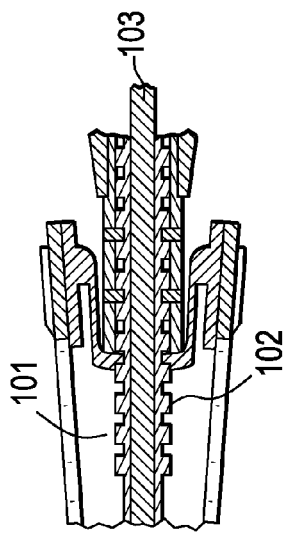

Therefore, in a first embodiment of this design, and now referring to FIGS. 11a-11c, there is provided the device of the present invention having a cannulated threaded shaft 101, with an inner push rod 103 that is smooth sliding. The outer shaft 101 has threads 102, and it can thread forward or backward within the central body. The inner push rod 103 is smooth, and it can slide back or be pushed (or impacted) forward, within the outer shaft.

Figure 12A:
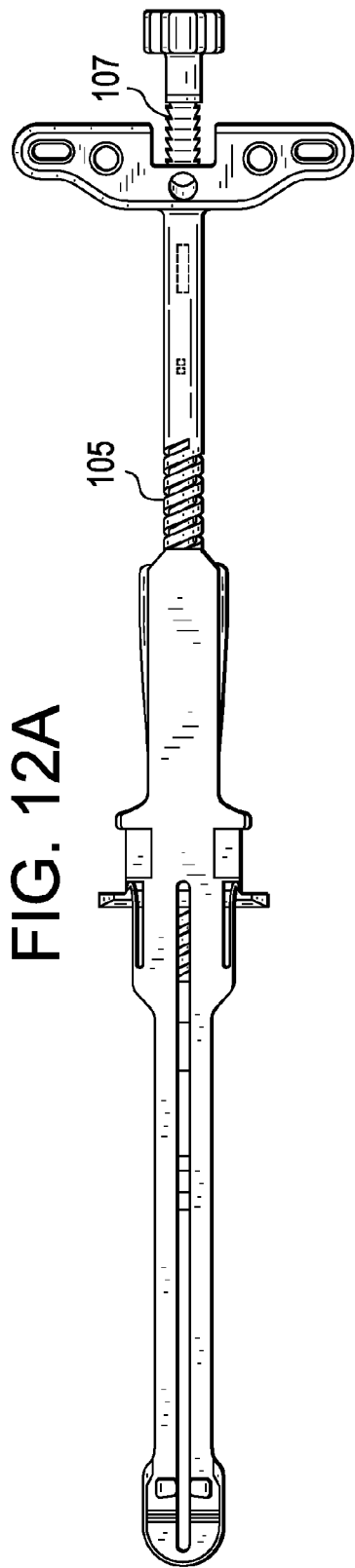
FIGS. 12a-12c disclose various views of a variation of a first embodiment of a shaft-pusher rod design.
Figure 12B:
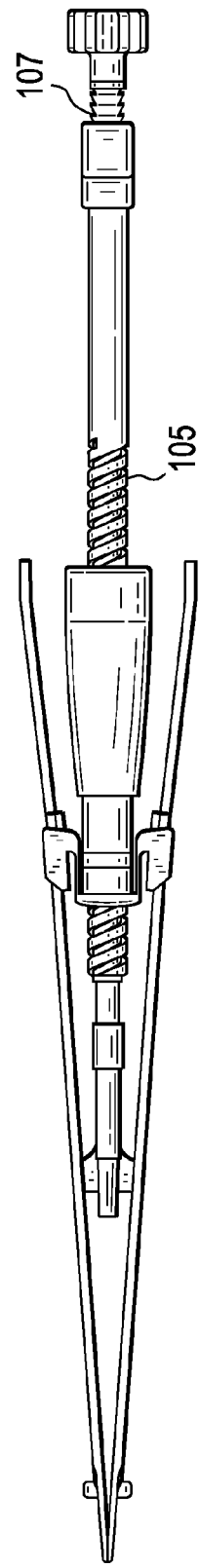
Figure 12C:
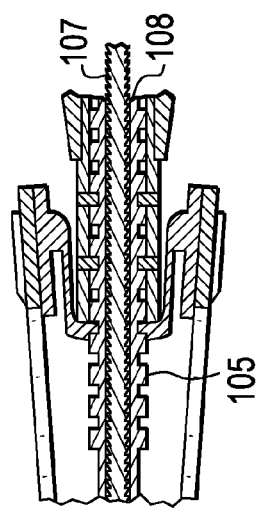

In a variation of the first embodiment of this design, the pushing rod can also have a plurality of teeth, such that it can "ratchet" forward when impacted, but not slide backward when the forward force is absent. "Ratcheting" forward of the pushing rod within the outer shaft allows forward sliding or impaction, with no sliding backward; but this still allows threading forward or backward with the outer shaft. In the variation of the first embodiment of this design, and now referring to FIGS. 12a-12c, there is provided the device of the present invention having a cannulated threaded shaft 105, with an inner push rod 107 having ratchet teeth. The outer shaft 105 is threaded, and it can thread forward or backward within the central body. The inner push rod 107 has ratchet teeth 108, and it can slide (or else ratchet forward only) within the outer shaft. It can have both an engaged mode and a free-sliding mode.

Figure 13A:
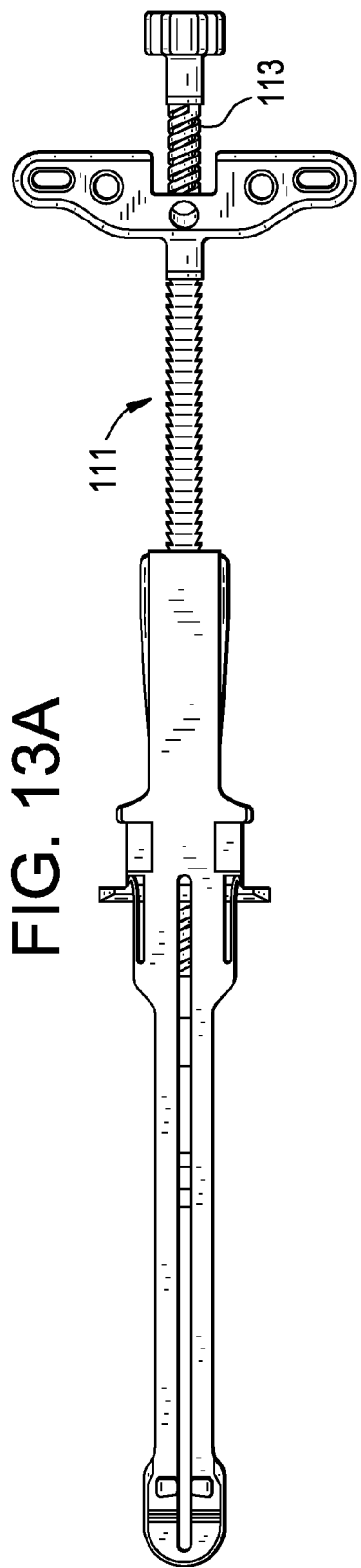
FIGS. 13a-13c disclose various views of a second embodiment of a shaft-pusher rod design.
Figure 13B:
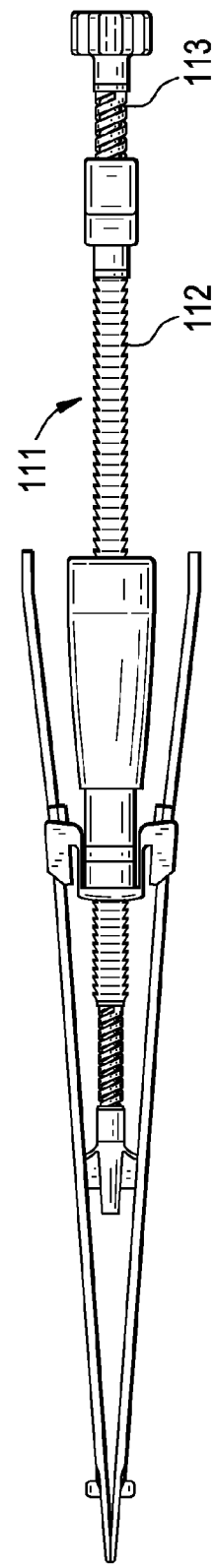
Figure 13C:
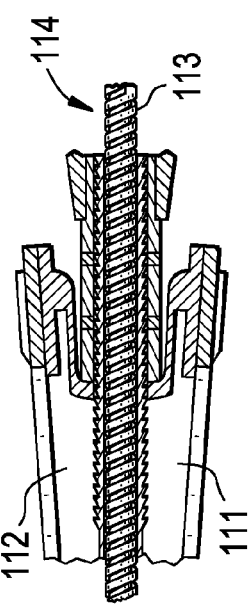

Alternatively, in a second embodiment of this design, the shaft can have ratchet teeth (instead of a thread, for advancing the shaft. Therefore, in some embodiments, the outer shaft has an outer surface having a set of teeth thereon, and the throughbore of the central body has a second threadform, wherein the first threadform or set of teeth of the shaft mates or engages with the teeth within the throughbore. In the second embodiment of this design, and now referring to FIGS. 13a-13c, there is provided the device of the present invention having a cannulated shaft 111 having ratchet teeth 112 and containing a threaded inner push rod. The outer shaft 111 has ratchet teeth 112 and it can slide (or else ratchet forward), within the central body. It can have both an engaged and a free-sliding mode. The inner push rod 113 has threads 114, and it can thread forward or backward within the outer shaft.

Alternatively, in a third embodiment of this design, the shaft can have ratchet teeth intergrated within the thread for advancing the shaft The threadform can have a "saw-tooth" shape, such that the threads also function as ratchet teeth, allowing the shaft to slide or ratchet forward, while also threading back and forth. In the third embodiment of this design, and now referring to FIGS. 14a-14c, there is provided the device of the present invention having a threaded inserter shaft 121 having a helical threadform 122 with angled ratcheting teeth. The threaded inserter shaft has ratcheting thread teeth, 127 and the teeth in the central body can be angled and movable apart, to allow the shaft to slide—or ratchet-forward (only) within the central body, due to the helical threadform on the shaft. The shaft can also thread forward or backward within the central body. The inserter shaft is threaded, such that it can thread forward or backward within the central body. But the thread teeth are also angled ratchet teeth, such that the shaft can also slide or ratchet forward. The blades 123 are flexibly coupled to the central body via a flexible bracket. The pusher block 125 is rotatably coupled to the ratcheting threaded shaft.

In some embodiments, the inserter further comprises: a pushing rod disposed within the cannula, wherein the pushing rod has a distal end forming a pusher block, and wherein the pusher block pushes the pair of sliding pusher brackets.

Similarly "ratcheting" forward with the outer shaft could provide the same capability, while the pushing rod could be threaded inside of the outer shaft—which can be constrained not to rotate. In that case, the pushing rod is essentially a "telescoping" assembly. And the converse configuration is also possible, whereby the outer shaft can slide forward—with or without a ratchet mechanism—while the inner pushing rod can be threadably advanced within the outer shaft. Finally, combining these features into one mechanism, an embodiment may have a central shaft whose threadform contains teeth which can not only be threadably advanced but also can ratched forward within the central body. In this way, "ratcheting" forward of the shaft allows forward sliding or impaction, with no sliding backward; but this feature still allows threading forward or backward with the outer shaft.

As the implant enters the intervertebral disc space, the inserter of the present invention can operate to allow the blades to automatically retract from the spine when fins on said pusher blocks make contact with the vertebral body. In some embodiments of the spinal implant inserter of the present invention, and now referring back to FIG. 8, there is a vertebral stop 75 extending from the outer surface 76 of each distal end portion of each blade; and these stops limit the forward position of the blades. Similarly, the pusher block 45 of FIG. 4 may contain corresponding vertebral stops 46, which stop the forward motion of the implant, such that subsequent actuation of the device serves to push the blades rear-ward relative to the implant and out of the spine. In other embodiments of the present invention, and now referring to FIG. 9c, the sliding pusher brackets 69 could also have such vertebral stops 73 located on the outside surfaces of the blades (which as in FIG. 6 may be narrower in the middle and wider at the tips. Such stops 73 could also protrude forward of their attachment point to the rest of the sliding bracket, so the blade tips can remain wider than the width between the fins where the pusher bracket wraps around the blade.

Thus, in some embodiments of the present invention, each blade can have a sliding pusher-bracket which bears against or advances the implant—which is between the blades—and then also contacts the vertebral body on the "outside" of the two blades. This eliminates the need to interrupt the blades with grooves or slots, since each sliding pusher-bracket can fit onto the outside of the blade on which it slides.

Now referring to FIG. 10a, there is provided a pair of blades of the present invention having a second embodiment of a sliding pusher bracket therebetween. The sliding pusher bracket assembly 85 comprises a pair of annular rings 87 that wrap around the respective blades, each having a central band 89 that connects the two annular rings with a slot 91 extending along the band, and a fin 95 attached to the respective rings that act as vertebral stops, and a central pusher 93 slidably attached to the slot in the band.

Figure 10B:
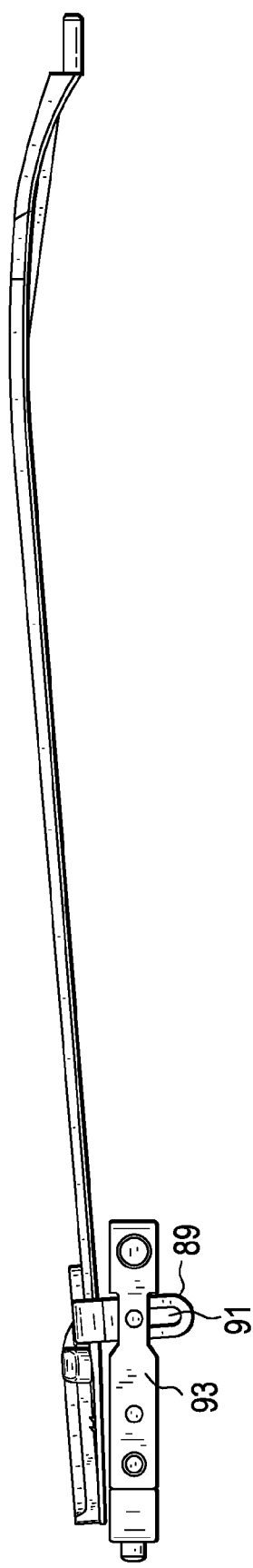
FIGS. 10 a through d disclose various views of blades of the present invention associated with a second embodiment of a sliding pusher bracket.

Now referring to FIG. 10b, there is provided the pair of blades and partial sliding pusher bracket of FIG. 10a, wherein the lower blade, ring and fin have been removed in order to provide a more clear picture of the central band 89 that connects the annular rings and the slot 91 extending along the band.

Figure 10C:
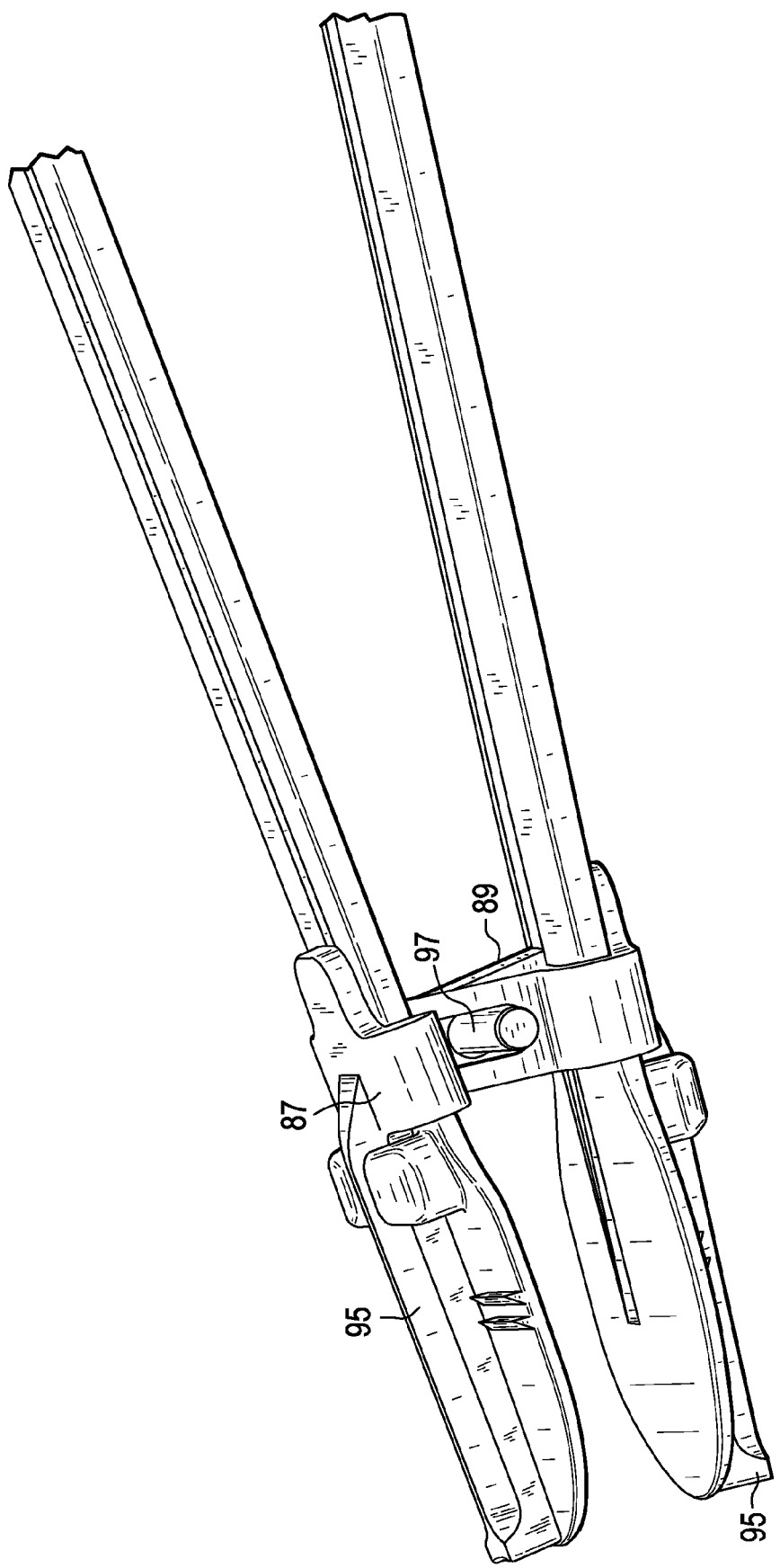

Now referring to FIG. 10c, there is provided an additional view of the pair of blades of the present invention showing a partial sliding pusher bracket therebetween, wherein the central band of the bracket includes a pin 97 extending transversely from the band. The pusher (not shown) can have a corresponding through-hole in which the pin 97 can ride, thereby providing sliding movement in a direction transverse to the blades.

Now referring to FIG. 10d, there is provided a pair of blades of the present invention having the second embodiment of a sliding pusher bracket therebetween, wherein distal 98, intermediate 99 and proximal 100 portions of the blades are also shown.

Although the present invention is preferably used for anteriorly inserting intervertebral spinal implants, it may also be used for either posteriorly, laterally, posterolaterally or anterolaterally inserting intervertebral spinal implants as well.

Other details and features of the device can be gleaned from the images contained in this document, and can be inferred by someone skilled in the art of designing or using such a device.

We claim:

1. A vertebral body implant inserter, comprising:
   a) a elongated central body having a distal end, a proximal end, an outer surface, a longitudinal throughbore therethrough, and a pair of leaf spring members extending from the outer surface,
   b) a pair of blades having a distal end portion and a base portion, the base portion of each blade detachably coupled to at least one of said spring members,
   c) a shaft advanceable within the throughbore, the shaft having an outer surface having a threadform thereon,
   wherein the shaft comprises an assembly having a cannulated outer shaft member and an inner push-rod movable therein,
   wherein the shaft has an outer surface having a first threadform thereon, and the throughbore of the central body has a second threadform thereon, wherein the first threadform of the shaft mates with the second threadform.

2. The inserter of claim 1 wherein the shaft has an outer surface having a first threadform thereon, and the throughbore of the central body has a set of teeth thereon, wherein the first threadform of the shaft mates with the set of teeth.

3. The inserter of claim 1 wherein the distal end portion of each blade has a vertebral stop.

4. The inserter of claim 3 wherein the distal end portion of each blade has at least one tooth extending transversely distal to the vertebral stop.

5. The inserter of claim 1 wherein each blade further has an intermediate portion, and wherein the distal end portion has a width that is greater than a width of the intermediate portion.

6. The inserter of claim 1 wherein the pair of spring members extending from the outer surface define a bracket.

7. The inserter of claim 1 wherein the inner push-rod contains a set of ratchet teeth adapted to bias the push-rod for distally forward motion within said shaft.

8. The inserter of claim 1 wherein the threadform of the shaft's outer surface comprises a series of angled protrusions adapted to bias the shaft for distally forward motion within the central body.

9. The inserter of claim 8 wherein the throughbore of the central body has a set of teeth thereon, wherein the teeth of the central body are movably adapted to permit either threadable or forwardly-linear motion of the shaft within the central body.

10. The inserter of claim 9 wherein the shaft has a set of ratchet teeth adapted to bias the shaft for distally forward motion within the central body.

11. The inserter of claim 1 wherein the blades are pivotally mounted.

12. The inserter of claim 1 wherein the blades are flexibly mounted.

13. The inserter of claim 1 wherein the blades contain a handle portion extending proximal from the base portion.

14. A vertebral body implant inserter, comprising:
   a) a elongated central body having a distal end, a proximal end, an outer surface, a first longitudinal throughbore therethrough,
   b) a bracket having i) an intermediate portion having a second longitudinal throughbore therethrough, ii) a first endportion, and iii) a second endportion, each endportion forming a spring member, the intermediate portion contacting the distal end of the central body so that the first longitudinal throughbore aligns with the second longitudinal throughbore,
   c) a pair of blades having a distal end portion and a base portion, the base portion of each blade detachably coupled to a respective spring member,
   d) a shaft slidable within the first longitudinal throughbore, the shaft having an outer surface having a threadform thereon,
   wherein each end portion of the bracket includes a proximally extending handle portion adapted for grasping the inserter,
   wherein the blades are adapted so that only their distal end portions contact each other.

15. The inserter of claim 14 wherein each blade has an inside surface containing a groove or raised ridge adapted for keeping the implant centered during insertion.

16. The inserter of claim 15 further comprising a pushing rod slidable within a cannula of the shaft, wherein the pushing rod is longer than the shaft so that the pushing rod can slide back and forth within the shaft, and allowing a proximal end of the pushing rod to be directly impacted distally.

17. The inserter of claim 16 wherein the distal end of each blade is tapered to narrow distally, thereby, allowing the blades to fit into a narrower space when they are brought together.

18. The inserter of claim 16 wherein the distal end of each blade comprising a vertebral stop adapted to stop the distal motion of the implant, such that subsequent actuation of the inserter pushes the blades rear-ward relative to the implant and out of the spine.

19. The inserter of claim 15 further comprising a pushing rod slidable within a cannula of the shaft, wherein the pushing rod has a plurality of teeth.

20. The inserter of claim 19 wherein the teeth are adapted to allow the pushing rod to ratchetedly advance distally when impacted by a distally directed force, but not slide proximally when the distally directed force is absent.

21. The inserter of claim 14 wherein each blade has a handle extension that extends proximally from the base portion and is adapted for grasping the inserter.

22. The inserter of claim 14 wherein each blade has a handle extension that extends proximally from the base portion and is adapted for providing distraction, whereby squeezing the handle extensions causes the blades to pivot about the bracket.

23. The inserter of claim 14 wherein the shaft comprises an axial cannula.

24. The inserter of claim 23 wherein the inserter further comprises:
   e) a pushing rod disposed within the cannula.

25. The inserter of claim 24 wherein the pushing rod has a distal end forming a pusher block.

26. The inserter of claim 14 wherein the bracket is spring-loaded.

27. The inserter of claim 26, wherein each bracket further comprises a vertebral stop extending from an annular ring.

28. A vertebral body implant inserter, comprising:
   a) a elongated central body having a distal end, a proximal end, an outer surface, a longitudinal throughbore therethrough, and a pair of leaf spring members extending from the outer surface,
   b) a pair of blades having a distal end portion and a base portion, the base portion of each blade detachably coupled to at least one of said spring members,
   c) a shaft advanceable within the throughbore, the shaft having an outer surface having a threadform thereon,
   d) a pair of sliding pusher brackets, each bracket comprising an annular ring and a fin protruding from the ring, wherein each annular ring is wrapped around a respective blade,
   wherein the shaft has an outer surface having a first threadform thereon, and the throughbore of the central body has a second threadform thereon, wherein the first threadform of the shaft mates with the second threadform
   wherein the threadform of the shaft's outer surface comprises a series of angled protrusions adapted to bias the shaft for distally forward motion within the central body,
   wherein the teeth of the central body are movably adapted to permit either threadable or forwardly-linear motion of the shaft within the central body.

29. The inserter of claim 28 wherein the inserter further comprises:
   e) a pushing rod disposed within the cannula, wherein the pushing rod has a distal end forming a pusher block, and wherein the pusher block pushes the pair of sliding pusher brackets.

30. A vertebral body implant inserter, comprising:
   a) a elongated central body having a distal end, a proximal end, an outer surface, a longitudinal throughbore therethrough, and a pair of spring members extending from the outer surface,
   b) a pair of blades having a distal end portion and a base portion, the base portion of each blade detachably coupled to a respective spring member,
   c) a shaft slidable within the throughbore, the shaft having an outer surface having a series of angled protrusions thereon, adapted to bias the shaft for distally forward motion within the central body,
   wherein advancing the shaft pushes the blades apart,
   wherein the shaft comprises an assembly having a cannulated outer shaft member and an inner push-rod movable therein,
   wherein the inner push-rod has an outer surface having a first threadform thereon, and the cannula of the outer shaft has a second threadform thereon, wherein the first threadform of the push-rod mates with the second threadform.

31. A vertebral body implant inserter, comprising:
   a) a elongated central body having a distal end, a proximal end, an outer surface, a longitudinal throughbore therethrough, and a pair of spring members extending from the outer surface,
   b) a pair of blades having a distal end portion and a base portion, the base portion of each blade detachably coupled to a respective spring member,
   c) a shaft slidable within the throughbore, the shaft having an outer surface having a series of angled protrusions thereon, adapted to bias the shaft for distally forward motion within the central body,
   wherein advancing the shaft pushes the blades apart,
   wherein the shaft comprises an assembly having a cannulated outer shaft member and an inner push-rod movable therein wherein the inner push-rod has an outer surface having a first threadform thereon, and the cannula of the outer shaft has a set of teeth thereon, wherein the first threadform of the push-rod mates with the set of teeth.

* * * * *